US011866245B2

(12) United States Patent
Luke et al.

(10) Patent No.: US 11,866,245 B2
(45) Date of Patent: Jan. 9, 2024

(54) DISPENSABLE SUBSTANCE CONTAINERS

(71) Applicant: HEWLETT-PACKARD DEVELOPMENT COMPANY, L.P., Spring, TX (US)

(72) Inventors: Jeff Luke, Boise, ID (US); Sean Daniel Fitzgerald, Boise, ID (US); Mathew Lavigne, Boise, ID (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 736 days.

(21) Appl. No.: 16/978,525

(22) PCT Filed: May 21, 2018

(86) PCT No.: PCT/US2018/033610
§ 371 (c)(1),
(2) Date: Sep. 4, 2020

(87) PCT Pub. No.: WO2019/226145
PCT Pub. Date: Nov. 28, 2019

(65) Prior Publication Data
US 2020/0399046 A1 Dec. 24, 2020

(51) Int. Cl.
*B65D 83/00* (2006.01)
*B41J 2/175* (2006.01)

(52) U.S. Cl.
CPC ...... *B65D 83/0022* (2013.01); *B41J 2/17506* (2013.01)

(58) Field of Classification Search
CPC .................. B65D 83/0022; B41J 2/17506
See application file for complete search history.

(56) References Cited

U.S. PATENT DOCUMENTS

| 5,372,071 A | 12/1994 | Richards et al. |
| 5,489,976 A | 2/1996 | Ichikawa |
| 5,706,870 A | 1/1998 | Maerzke |
| 5,887,633 A | 3/1999 | Yale et al. |
| 7,060,049 B2 | 6/2006 | Trombley, III et al. |
| 7,328,986 B2 * | 2/2008 | Wang ............... B41J 2/17506 347/85 |
| 7,789,855 B2 | 9/2010 | Liu |
| 8,562,571 B2 * | 10/2013 | Mudd ............... A61M 5/3158 604/218 |
| 2006/0041231 A1 | 2/2006 | Pressly et al. |

(Continued)

FOREIGN PATENT DOCUMENTS

| FR | 1083538 A | 1/1955 |
| WO | WO0226502 A1 | 4/2002 |

*Primary Examiner* — Jason K Niesz
(74) *Attorney, Agent, or Firm* — Foley & Lardner LLP

(57) ABSTRACT

A dispensable substance container may include an elongate body encompassing a lumen, wherein the lumen is to contain the dispensable substance; a dispensable; substance dispensing nozzle attached to a first end on the elongate body; a sealing material within the lumen, wherein the sealing material is moveable, by a pushrod, within the lumen to push the dispensable substance out the dispensing tip; and a structurally compromised portion of the elongate body extending along a length of the elongate body, wherein the elongate body is to be severed along the structurally compromised portion by the pushrod.

15 Claims, 6 Drawing Sheets

(56) References Cited

U.S. PATENT DOCUMENTS

| 2006/0122561 A1* | 6/2006 | Ray | A61M 5/50 |
| | | | 604/110 |
| 2008/0188816 A1* | 8/2008 | Shimazaki | A61M 5/34 |
| | | | 604/240 |
| 2011/0137260 A1 | 6/2011 | Mudd | |
| 2014/0228804 A1 | 8/2014 | Castillo | |

* cited by examiner

DISPENSABLE SUBSTANCE CONTAINERS

CROSS REFERENCE TO RELATED APPLICATIONS

This application is a U.S. National Stage Application which claims the benefit under 35 U.S.C. § 371 of International Patent Application No. PCT/US2018/033610 filed on May 21, 2018, the contents of which are incorporated herein by reference.

BACKGROUND

Containers may be utilized to contain, store, and/or transport substances. Containers may contain substances that may be dispensed from the containers. For example, some containers may be utilized to dispense the dispensable substances into other containers. Containers that may be utilized to dispense the dispensable substances into another container may include a structure to not only store, but to facilitate the transfer of the dispensable substance. For example, a container that may be utilized to dispense dispensable substances may include a syringe.

DETAILED DESCRIPTION

Figure 1:
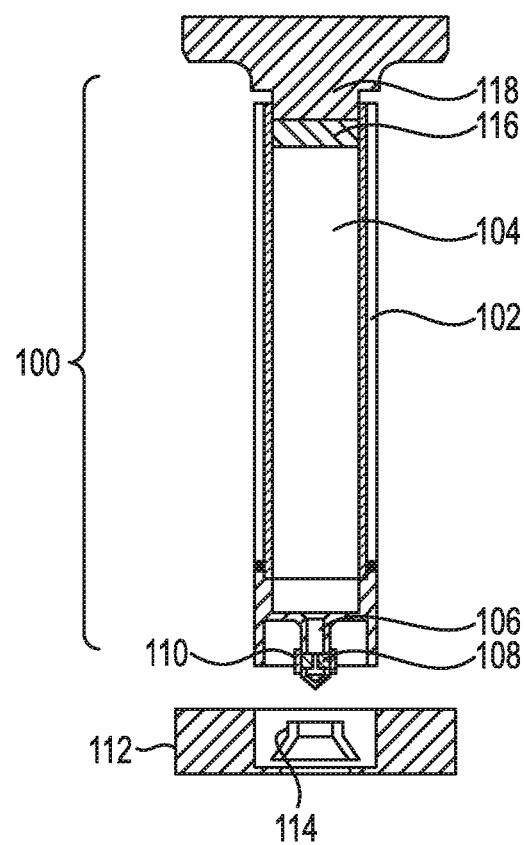
FIG. 1 illustrates a cross-sectional view of a dispensable substance container according to the present disclosure.

A container, such as a syringe, may include a cylindrical tube or barrel. The barrel may be utilized to store a dispensable substance. At one end of the barrel, the syringe may include a nozzle or tubing to direct flow out of the barrel. The barrel may be open at the opposing end, except for a plunger or piston that fits tightly within the barrel effectively sealing the dispensable substance off from escaping that end of the barrel.

Such a container may operate as a single-acting reciprocating pump. For example, one side of the piston may engage the dispensable substance and/or a fluid such as a gas in the barrel. The piston may be linearly pulled and/or pushed along the inside of the barrel causing the container to dispense or take in a substance through the nozzle or tubing.

In order to utilize a full volume of the barrel, the piston may be linearly pushed or pulled along the full length of an elongate barrel. As such, the piston may have a length that is at least as long as the elongate barrel to allow the piston head to read the end of the barrel proximate the nozzle, in order to fully dispense the contents thereof. Since a portion of the piston may be actuated by a user outside of the barrel, the length of the piston may exceed the length of the barrel.

As such, when the barrel of the syringe is full of a dispensable substance, the piston may be sticking out of the barrel by a length at least as long as, and in some cases longer than, the length of the barrel itself. Accordingly, the length of the syringe inclusive of the piston is at least double the barrel length when the barrel is full of a dispensable substance. Additional length may make shipping or otherwise transporting the syringe more difficult. For example, a long syringe may be more awkward and/or costly to transport. A long syringe may be more prone to damage than a shorter one on account of the additional length being exposed, Additionally, a long syringe may not fit into small spaces with insufficient clearance for the length. In some examples, a syringe with a shorter barrel and correspondingly dimensioned piston may be utilized to fit into small spaces. However, the volume of the syringe may be reduced when its length is reduced. As such, length and/or volume restrictions associated with utilizing syringe-like containers in confined spaces may render such containers unsuitable for particular applications.

In contrast, examples of the present disclosure may include a dispensable substance container that does not utilize a piston that is a same or longer length than an elongate body of the container. For example, examples of the present disclosure may include a system. The system may include an elongate body including a wall encompassing a lumen, wherein the lumen is to contain a dispensable substance, and a structurally compromised portion of the wall extending longitudinally along a length of the elongate body. The system may include a pushrod, the pushrod including a rod body to seat within the lumen, wherein the rod body is moveable longitudinally through the length of the elongate body and an extension from the rod body to shear a gap into the structurally compromised portion of the wall when the rod body is moved through the lumen in response to a force applied to a handle outside of the wall and connected to the rod body through the gap.

FIG. 1 illustrates a cross-sectional view of a dispensable substance container 100 according to the present disclosure. The dispensable substance container 100 may include an elongate body 102. The elongate body 102 may include a wall that defines and/or encompasses a lumen 104, The lumen 104 may be filled with, refilled with, and/or contain a dispensable substance.

The elongate body 102 may include a wall that may have any geometry and/or define a lumen 104 of any geometry. In an example, the elongate body 102 may be a barrel or tube that is cylindrically shaped. In some examples the lumen 104 may be cylindrically shaped. In other examples, the elongate body 102 and/or the lumen 104 may have square, oval, triangular, etc. geometries.

The dispensable substance that may be contained within the lumen 104 may be a solid, a liquid, and/or a gas. The dispensable substance may be a substance that may be contained in and/or expelled from the elongate body 102. That is, the dispensable substance may flow into, out of, and/or through the elongate body 102 under external pressure. For example, the dispensable substance may be a printing substance. A printing substance may include a liquid printing ink, a toner powder, a three-dimensional printing substance, etc.

The dispensable substance container 100 may be sealed from the external environment. For example, the elongate body 102 and its contents may be sealed from the external environment at a first end. For example, a first end of the elongate body 102 may include a dispensable substance dispensing nozzle 106. The dispensing nozzle 106 may be attached to the first end of the elongate body 102. For example, the dispensing nozzle 106 may be a part that is separate from the elongate but is fixed to the elongate body 102 by fastening means. In other examples, the dispensing nozzle 106 and the elongate body 102 may be two portions of a single molded assembly.

The dispensing nozzle 106 may include a wall shaped to control the direction and/or characteristics of the flow of the dispensable substance from the dispensable substance container 100. In some examples, the walls of the dispensing nozzle 106 may define a lumen that has a smaller volume and/or diameter than the elongate body 102. In some examples, the walls of the dispensing nozzle 106 may be tapered.

The dispensing nozzle 106 may include an opening 108. The opening 108 may be one of a plurality of openings in the dispensing nozzle 106. The opening 108 may include an opening into a lumen of the dispensing nozzle 106. Since the dispensing nozzle 108 may be in fluid communication with the elongate body 102, the opening 108 may be an opening where a dispensable substance expelled from the elongate body 102 is dispensed.

In some examples, the dispensing nozzle 106 may include a sleeve 110. The sleeve 110 may include a body encompassing the body of the dispensing nozzle 106 and obstructing the opening 108 when in place. In some examples, the sleeve 110 may be attached to the dispensing needle via a frangible attachment and/or itself be frangible. When the dispensable substance container 100 is joined with a dispensable substance receiving container 112, a protrusion 114 from the dispensable substance receiving container 112 may break the sleeve 110 free from the dispensing nozzle 106 and translate the sleeve 110 away from the opening 108 allowing the opening 108 to be utilized to dispense the dispensable substance.

The dispensable substance receiving container 112 may include a container for receiving and/or storing the dispensable substance that is dispensed from the dispensable substance container 100. In some examples, the dispensable substance container 100 and the dispensable substance receiving container 112 may include specialized complementary structures that facilitate the mating of the two together and introduce fluid communication between the two. That is, the dispensable substance container 100 and/or the dispensable substance receiving container 112 may include complementary mating mechanisms which slide together in an interlocking fashion to mate the two together by aligning the dispensing nozzle with an opening in a dispensing substance receiving container 112.

In some examples, the dispensable substance receiving container 112 may include a printing substance reservoir or cartridge. For example, the dispensable substance receiving container 112 may be a portion of a printing device that serves as a reservoir for the dispensable printing substance until a time when the dispensable printing substance is to be utilized for a printing operation of the printing device.

The elongate body 102 and its contents may also be sealed from the external environment at a second end. For example, a second end of the elongate body 102 may include a sealing material 116. The sealing material 116 may include a gasket, such as a rubber or plastic gasket. The sealing material 116 may be utilized as a plunger or piston head may be utilized in a syringe. For example, the sealing material 116 may seat tightly within the elongate body 102 engage the walls of the elongate body 102. The sealing material 116 may be moveable along an entire length of the elongate body 102. For example, the sealing material 116 may engage the walls of the elongate body 102 along the entire inner circumference of such walls such that the sealing material may wipe the inner surface walls of the elongate body 102 and advance a dispensable substance through the elongate body 102 without allowing the dispensable substance to slip past the sealing material 116 as the sealing material 116 is advanced through the elongate body 102.

As described above, the sealing material 16 may be moveable throughout the elongate body 102 to advance a dispensable substance within the elongate body 102 through the elongate body 102, through the dispensing nozzle 106, and out of the opening 108. While gravity may assist this movement, additional force loads may be transferred to the dispensable substance in the lumen 104 of the elongate body 102 via the sealing material 116. However, this may mean that a force load may be applied to the sealing material 116. In some examples, the force load may be introduced by a user of the dispensable substance container 100. The force load may be a force load of a magnitude to overcome a pressure within the lumen 104 and advance the dispensable substance and/or the sealing material 116.

A force load may be introduced to the dispensable substance in the lumen 104 of the elongate body 102 and/or the sealing material 116 by a pushrod 118. A pushrod 118 may be a separate component from and/or integrated with the elongate body 102. The pushrod 118 may be a separate component from and/or integrated with the sealing material 116. The pushrod 118 may be depressed by a user utilize a force load. The pushrod 118 may transfer the force load 118 to the sealing material 116 and/or the dispensable material within the lumen 104 by advancing the sealing material 116 through the lumen 104 of the elongate body 102.

Unlike other syringes, the pushrod 116 of examples of the present disclosure may have a length that is less than the length of the elongate body 102 and/or the lumen 104. In some examples, the pushrod 116 may have a length that is less than half the length of the elongate body 102 and/or the lumen 104. In some examples, the pushrod 116 may have a length that is less than one-quarter the length of the elongate body 102 and/or the lumen 104. In some examples, the pushrod 116 may have a length such that if it were fully advanced into the lumen 104 until a portion of the pushrod 116 (having a width greater than the width of the lumen 104 of the elongate body 102) first encountered a wall of the elongate body 102, the pushrod 102, the pushrod 118 and/or the sealing material may not reach the bottom of the lumen 104 and/or the elongate body 102. Additionally, in such examples, less than the entire contents or none of the contents of the lumen 104 may be expelled from the elongate body 102.

In contrast to a reliance on a relatively longer pushrod 118 that itself as long as or longer than the length of the lumen 104 and/or the elongate body 102 to dispense the dispensable fluid from the lumen 104, examples of the present disclosure may include a structurally compromised portion of the elongate body 102 extending along a length of the elongate body 102 where the elongate body 102 is to be severed along the structurally compromised portion. In some examples, the structurally compromised portion of the elongate body 102 may be severed by a bladed portion of the pushrod 118 as discussed in further detail below.

As used herein, the term "structurally compromised" may refer to a portion of the elongate body 102 that is engineered to separate under specific force loads. In some examples, a structurally compromised portion may be structurally weakened or structurally modified relative to other portions of the elongate body 102.

A "structurally weakened" portion may be a portion of the elongate body 102 may be a portion that has a reduced thickness, a reduced shear strength, different material properties, modified chemical composition, perforations, scribing, scoring, abrasions, etching, heat treatment, etc. that renders the structurally compromised portion relatively more prone or susceptible (e.g., less force load involved) to separation than adjacent portions of the elongate body 102.

A "structurally modified" portion may include a portion of elongate body 102 that includes a structural feature or architecture that may be engineered to be separated without cutting through the elongate wall 102. Rather, the structural feature may allow two portions to be pushed apart to achieve separation. For example, a structural modification may include an overlap of elongate body 102 walls. For example, at composite walls of the elongate body 102 may create an overlap localized within the structurally compromised portion. The overlap may establish and/or maintain a seal between the content within the elongate body 102 and the external environment. The structurally modified portion may be separated at the overlap.

In some examples, the structurally compromised portion may not be structurally weakened and/or structurally modified relative to the other portions of the elongate body 102. That is, the elongate body 102 may have a substantially uniform thickness, chemical composition, shear strength, material properties, modifications, treatment, structural characteristics, etc. across the portions of the elongate body 102. In such examples, the elongate body 102 may be constructed of a substantially uniform material that is structurally strong and/or rigid enough to provide structural integrity to the dispensable substance container during filling, storing, transporting, and dispensing a dispensable substance from the dispensable substance container, but that is soft enough to be severed by application of a force load by a first projection of a pushrod within particular force load threshold values. As such, in some examples, the entire elongate body 102 may be structurally compromised since it is uniformly engineered to separate under specific force loads.

Figure 2:
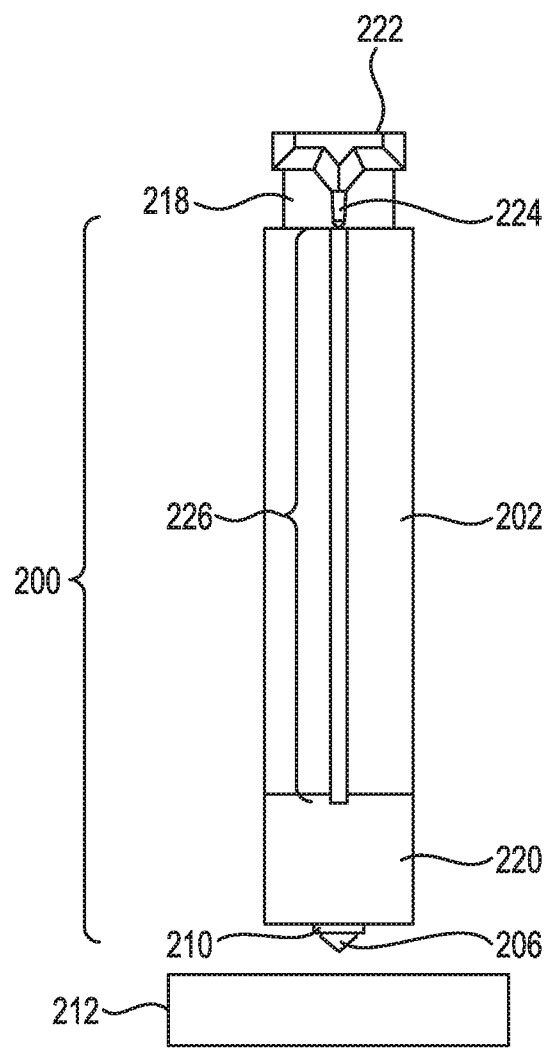
FIG. 2 illustrates a side view of a dispensable substance container according to the present disclosure.

FIG. 2 illustrates a side view of a dispensable substance container 200 according to the present disclosure. The dispensable substance container 200 may include an elongate body 202. The elongate body 202 may be a wall that defines and/or encompasses a hollow lumen within the wall. The elongate body 202 wall may include a plurality of portions and/or layers having different characteristics and/or properties as will be described in further detail below.

The dispensable substance container 200 may include a dispensing nozzle 206 and/or a mating mechanism 220 including walls encompassing the dispensing nozzle 206 to mate with a dispensable substance receiving container 212 in an interlocking fashion to align the dispensing nozzle 206 into the dispensable substance receiving container 212. Mating the dispensable substance container 200 with the dispensable substance receiving container 212 may cause a sleeve 210 that encompasses and obstructs openings in the dispensing nozzle 206 to break free from the dispensing nozzle and introduce fluid communication between the dispensable substance container 200 and the dispensable substance receiving container 212.

A dispensable substance within the lumen of the elongate body 202 may be influenced by the actuation of pushrod 218 into the lumen of the elongate body 202. As the pushrod 218, seated within the lumen of the elongate body 202, is pushed further into the lumen, the force load being applied to the pushrod 218 may be transferred to the contents of the lumen, causing the contents to advance through the elongate body 202 and/or exit the openings on the dispensing nozzle 206.

However, as described with respect to FIG. 1, the longitudinal length of the pushrod 218 may be less than the longitudinal length of the elongate body 202 and/or the longitudinal depth of the lumen defined thereby. Since the pushrod 218 may be dimensioned to fit snuggly, but moveably, within the lumen of the elongate body 202, any projection from the body of the pushrod 218 would prevent the pushrod 218 from descending any further into the depths of the lumen within the elongate body 102 once said projection encountered a wall of the elongate body 102. As illustrated, the pushrod 218 may include a first projection 222 emanating from the central body of the pushrod 218 that will encounter the wall of the elongate body 202 as the pushrod is advanced into the lumen of the elongate body 202. The first projection 222 may include a wedge and/or blade portion 224. Specifically, the first projection 222 may include a wedge and/or blade portion 224 with a leading and/or cutting edge oriented down toward the wall of the elongate body 202.

The elongate body 202 may have distinct portions. For example, the elongate body 202 may include a structurally compromised portion 226. The structurally compromised portion 226 may extend linearly along a longitudinal length of the elongate body 206. That is, the structurally compromised portion 226 of the elongate body 206 may include a portion of the elongate body 202 such as a strip that runs continuously from proximate a first end of the elongate body 202 to the second end of the elongate body 202.

The structurally compromised portion 226 may include a portion of the wall of the elongate body 202 that is engineered to have less structural integrity and/or resistance to cutting and/or shear forces than a remainder of the wall of the elongate body 202. For example, the structurally compromised portion 226 of the wall of the elongate body 202 may be a portion of the wall of the elongate body 202 with a thickness that is less than a thickness of a second portion of the wall of the elongate body 202. That is, the structurally compromised portion 226 of the elongate body 202 may include a portion of the elongate body 202 with relatively thinner walls than the remainder of the wall of the elongate body 202. The relatively thinner walls of the structurally compromised portion 226 may be relatively more prone or susceptible to (e.g., less force load required) cutting and/or shear forces than the thicker walled portions.

In some examples, the structurally compromised portion 226 of the wall of the elongate body 202 may be a portion of the wall of the elongate body 202 that is constructed of a different material than the remainder of the wall of the elongate body 202. That is, the structurally compromised portion 226 of the wall of the elongate body 202 may include a strip of the wall of the elongate body 202 that is made of a material with different characteristics or properties than the material from which the other portions of the wall of the elongate body 202 are constructed. Specifically, the structurally compromised portion 226 of the wall of the elongate body 202 may be made up of a material that is structurally strong enough to withstand the forces associated with filling, storing, transporting, and dispensing a dispensable substance from the dispensable substance container 200, but structurally weak and/or soft enough to be severed by the cutting and/or shear forces introduced by the wedge and/or blade portion 224 as described in further detail below.

In some examples, the structurally compromised portion 226 of the wall of the elongate body 202 may be a portion of the wall of the elongate body 202 that is structurally weakened. For example, the structurally compromised portion 226 of the wall of the elongate body 202 may be a portion of the wall of the elongate body 202 that is structurally weakened by perforating, scribing, scoring, abrading, etching, chemically modifying, heat treating, etc. such that the structurally compromised portion 226 of the wall of the elongate body 202 is relatively more prone or susceptible to (e.g., less force load required) cutting and/or shear forces than the other portions of the wall of the elongate body 202 that are not structurally weakened in the same manner.

Additionally, the wall of the elongate body 202 may have at least an inner layer and an outer layer. The inner layer of the wall of the elongate body 202 may be the layer of the wall of the elongate body 202 that is open to and/or contacts a dispensable substance within the lumen of the elongate body 202. The outer layer of the wall of the elongate body 202 may be the layer of the wall of the elongate body 202 that is opposite the inner layer and/or is open to environment.

In some examples, the inner layer and the outer layer of the wall of the elongate body 202 may be made up of materials with differing properties and/or characteristics. For example, the inner layer may be made up of a relatively softer and/or less structurally rigid material to provide a smooth interface across which to move the pushrod 218 and/or a sealing material. Such a material relatively more prone or susceptible to (e.g., less force load required) cutting and/or shear forces than the material of the outer layer. The outer layer may provide more structurally rigidity but may be more resistant to cutting and/or shear forces. In such examples, the structurally compromised portion 226 of the wall of the elongate body 202 may be a portion of the outer wall of the elongate body 202 that is structurally weakened as described above. That is, since the inner layer is already relatively susceptible to cutting and/or shear forces, it may not be structurally weakened because the structurally weakening process may modify its characteristics or properties such that it is no longer sealing in the dispensable substance, providing a smooth and/or soft surface to facilitate the flow of the dispensable substance, and/or facilitating the movement of the sealing material and/or the pushrod 218 within the lumen of the elongate body 202. However, the structural integrity of the structurally compromised portion 226 may be effectuated by weakening the outer layer to produce a portion that is susceptible on the inner wall and the outer wall to cutting and/or shear forces.

The structurally compromised portion 226 of the elongate body 202 extending longitudinally along the length of the elongate body 202 may be a portion of the elongate body 202 that is to be severed, That is, the elongate body 202 may be engineered to be severed along and/or within its structurally compromised portion 226, hence the imposition of susceptibility to cutting and/or shear forces within the structurally compromised portion 226. Specifically, the elongate body 202 may be engineered to be severed along and/or within its structurally compromised portion 226 by the wedge and/or blade portion 224 of the first projection 222 emanating from the central body of the pushrod 218. For example, the leading and/or cutting edge of the wedge and/or blade portion 224 may be oriented straight down or at an angle toward the wall of the elongate body 202. The leading and/or cutting edge of the wedge and/or blade portion 224 may be aligned with the structurally compromised portion 226 of the elongate body 202, For example, the leading and/or cutting edge of the wedge and/or blade portion 224 may be aligned such that when the pushrod 218 is actuated into and/or through the lumen of the elongate body 202, the wedge and/or blade portion 224 may travel within and/or sever within a channel defined by the structurally compromised portion 226.

The pushrod 218, despite being shorter than the length of the lumen and/or the elongate body 202 may be advanced along the entirety of the lumen and/or the elongate body 202. This may be because the wedge and/or blade portion 224 protruding from the pushrod 218 may continue to sever the structurally compromised portion 226 of the elongate body 202 from one end of the elongate body 202 to the other. The gap created between the severed portions of the elongate body 202 may accommodate the reminder of the of the first projection 222 emanating from the central body of the pushrod 218 which may move along with the pushrod 218, but through and outside of the elongate body 202. The reminder of the first projection 222 may provide a handle and/or shelf-like portion allowing a user to achieve and maintain a purchase on the first projection 222 while applying the force load to the pushrod 218 through the handle and/or shelf-like portion of the first projection 222 that may be utilized to move the pushrod 218.

However, it is contemplated that some examples of the present disclosure include dispensable substance containers that do not include a structurally compromised portion of the elongate body. That is, in some examples, the elongate body may be constructed of a uniform material with uniform characteristics and/or properties. For example, the elongate body may be a same material across its portions. A wall of the elongate body may be a same thickness across its portions. A wall of the elongate body may be subjected to the same treatments and/or processes across its portions. In such examples, the uniform material of the elongate body may be a material that is structurally strong and/or rigid enough to provide structural integrity to the dispensable substance container during filling, storing, transporting, and dispensing a dispensable substance from the dispensable substance container. Simultaneously, the uniform material of the elongate body may be a material that is soft enough to be severed by the wedge and/or blade portion of a first projection of a pushrod within particular force load threshold values. In these examples, advancing the pushrod through the lumen of an elongate body by applying a force load to the first projection causing the wedge and/or blade portion of the first portion of the pushrod to cut through the wall of the elongate body may operate in substantially the same way as described above. However, instead of selectively aligning the wedge and/or blade portion of a first projection of a pushrod with a structurally compromised portion of the elongate body, any portion along the longitudinal length of the elongate body may be cut through.

In some examples, the structurally compromised portion 226 may include a portion of overlapping elongate body 202 walls. For example, at the structurally compromised portion 226 composite walls of the elongate body 202 may create an overlap localized within the structurally compromised portion 226. The overlap may establish and/or maintain a seal between the content within the elongate body 202 and the external environment. In such examples, the wedge and/or blade portion 224 of the pushrod 218 may or may not have a wedge or blade shape. For example, the wedge and/or blade portion 224 may have a dimension and/or a geometry, wedge shaped or not, that causes separation of the sealing overlap at the structurally compromised portion 226 as the pushrod 218 is advanced within the elongate body 202.

For the purposes of this description, the structurally compromised portion 226 of the elongate body 202 may include any of the above examples including those where the structurally compromised portion 226 is structurally weakened, has relatively weaker structural characteristics than other portions the elongate body 202, and/or has similar or same structural characteristics of other portions of the elongate body 202 but is the channel where the elongate body 202 is cut.

In some examples, including examples where the structurally compromised portion 226 is structurally weakened and/or has relatively weaker structural characteristics than other portions the elongate body 202, the dispensable substance container 200 may include a sheath or guard portion. A sheath or guard portion may include a removable, rotatable, slide-able, etc. sheath or guard that covers at least the structurally compromised portion 226 of the elongate body 202. The sheath and/or guard portion may be fitted about and/or attached to the exterior of the elongate body 202 to cover at least the structurally compromised portion 226 prior to dispensing. The sheath and/or guard portion may provide structural reinforcement to at least the structurally compromised portion 226 of the elongate body 202. The sheath and/or guard portion may be removable and/or rotatable away from at least structurally compromised portion 226 and/or the channel where the wedge and/or blade portion 224 of the pushrod 218 will split the elongate body 202 immediately prior to dispensing. In this manner, the sheath and/or guard portion may reinforce and/or protect the structurally compromised portion 226 of the elongate body 202 from premature rupture, cutting, splitting, damage, etc. resulting from filling, storing, transporting, shipping, positioning, and/or handling the dispensable substance container 200.

Figure 3:
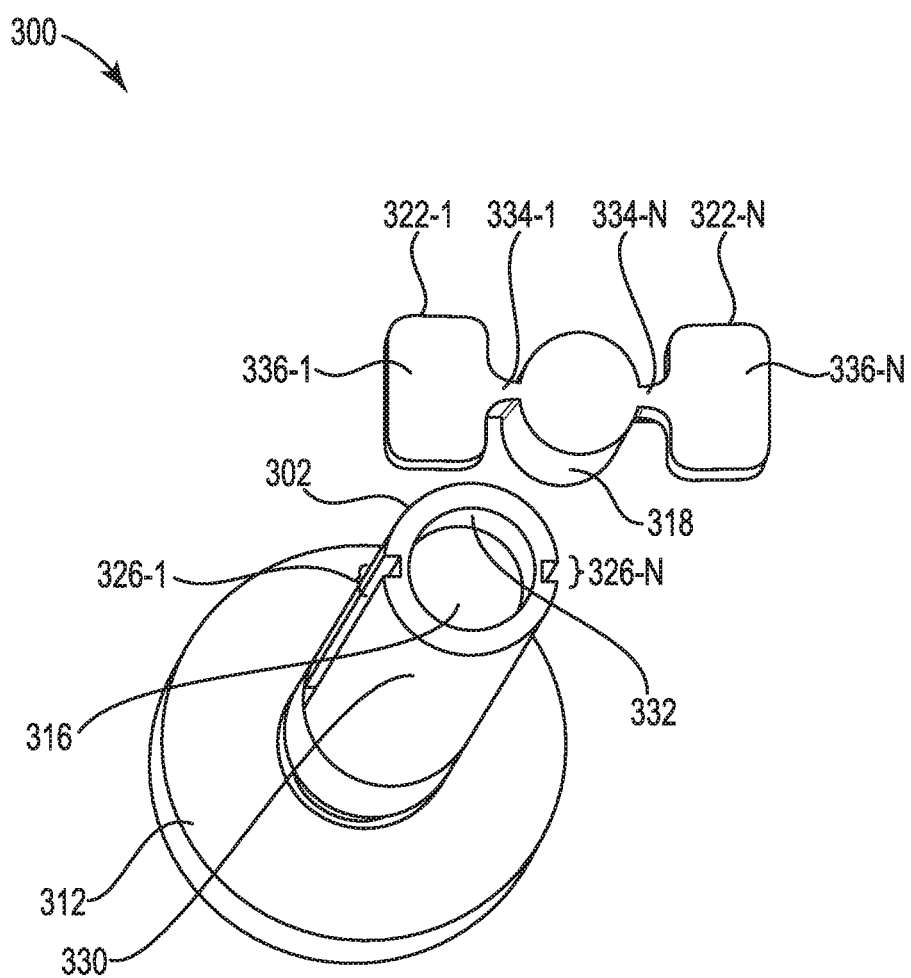
FIG. 3 illustrates a top view of a dispensable substance container according to the present disclosure.

FIG. 3 illustrates a top perspective view of a dispensable substance container 300 according to the present disclosure. The dispensable substance container 300 may include an elongate body 302. The elongate body 302 may include a wall that encompasses and defines a lumen within the elongate body 302. The wall of the elongate body 302 may have a width and/or thickness of material between an inner wall 332 and an outer wall 330 of the elongate body 302. The width and/or thickness of the wall of the elongate body may vary across portions of the elongate body 302.

For example, the elongate body 302 may include structurally compromised portions 326-1 . . . 326-N. The structurally compromised portions 326-1 . . . 326-N of the elongate body 302 may have a different width and/or thickness than the non-structurally compromised portions of the elongate body 302. For example, the width and/or thickness of the wall of the elongate body 302 at the structurally compromised portions 326-1 . . . 326-N may be thinner and/or less wide than the wall of the elongate body 302 at the non-structurally compromised portions.

The thinner structurally compromised portions 326-1 . . . 326-N may be portions of the wall of the elongate body to be severed by a wedge and/or blade portion of each of a plurality of projections 322-1 . . . 322-N radially extending outward from the central body of the pushrod 318. By aligning the wedge and/or blade portion of each of a plurality of projections 322-1 . . . 322-N, with the structurally compromised portions 326-1 . . . 326-N of the elongate body 302 and applying a force load to a handle portion of each of a plurality of projections 322-1 . . . 322-N the central body of the pushrod 318 may seat into the lumen of the elongate body 302 and advance through the lumen of the elongate body 302 as the wedge and/or blade portions sever the structurally compromised portions 326-1 . . . 326-N creating a gap in the wall of the elongate body 302 for the plurality of projections 322-1 . . . 322-N to span through and remain outside the lumen of the elongate body 302.

The pushrod 318 may contact and/or seat on top of a sealing material 316. Advancing the pushrod 318 may, in turn, advance the sealing material 316 and propel a dispensable substance within the lumen and under the sealing material 316 to be dispensed out of a dispensing nozzle into a dispensable substance receiving container 312. The pushrod 318 may be advanced by pressing on the plurality of projections 322-1 . . . 322-N. Each one of the plurality of projections 322-1 . . . 322-N may include a corresponding first portion 334-1 . . . 334-N and a corresponding second portion 336-1 . . . 336-N. The first portion 334-1 . . . 334-N may have a first width while the second portion 336-1 . . . 336-N may have a second width. Despite having differing widths, the first portion 334-1 . . . 334-N and the second portion 336-1 . . . 336-N may be continuous with each other and/or continuous with the central body of the pushrod 318. In some examples, the first portion 334-1 . . . 334-N may connect the second portion 336-1 . . . 336-N to the central body of the pushrod 318. In some examples, the width of the first portion 334-1 . . . 334-N may be less than the width of the second portion 336-1 . . . 336-N. As such, the first portion 334-1 . . . 334-N may be a portion having a width to fit within and a length to span through a gap created in the wall of the elongate body 302 by the blade mounted beneath the first portion 334-1 . . . 334-N. Further, the second portion 336-1 . . . 336-N may be a portion having a width and a length to be utilized as handles or pads upon which to apply a force load for advancing the pushrod 318.

Figure 4:
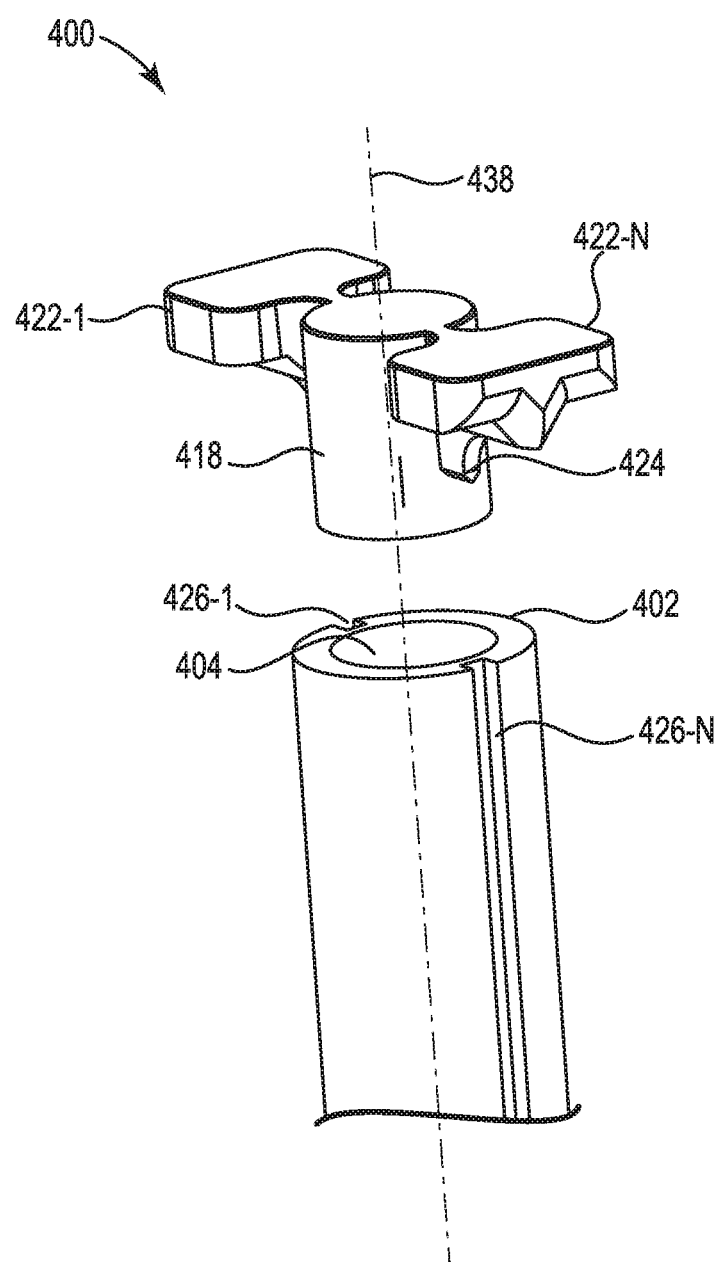
FIG. 4 illustrates a side view of a portion of a dispensable substance container.

FIG. 4 illustrates a perspective side view of a portion of a dispensable substance container 400. The dispensable substance container 400 may include an elongate body 402. The elongate body 402 may include a wall encompassing and defining a lumen 404 that may hold a dispensable substance. The elongate body 402 may include structurally compromised portions 426-1 . . . 426-N of the wall of the elongate body 402.

A pushrod 418 may be utilized to advance the printable substance through the elongate body 402. The central body of the pushrod 418 may include a cylindrically shaped rod dimensioned to seat snuggly but moveably within the lumen 404. However, the central body of the pushrod 418 may be any geometry that is a complementary geometry to the geometry of the lumen 404. However, a length of the pushrod along a longitudinal axis 438 may be less than a length of the lumen 414 and/or the elongate body 402 along the longitudinal axis 438.

However, a plurality of projections 422-1 . . . 422-N may emanate radially outward from the longitudinal axis 438 of the central body of the pushrod 418. The plurality of projections 422-1 . . . 422-N may extend from the central body of the pushrod 418 and outside of the wall of the elongate body 402 when the central body of the pushrod 418 is within the lumen 404 of the elongate body 402. That is, regardless how shallow or deep the pushrod 418 is seated into the lumen 404, the plurality of projections 422-1 . . . 422-N may stay outside of the central body of the pushrod 418.

Each of the plurality of projections 422-1 . . . 422-N may include a wedge and/or blade portion 224. The wedge and/or blade portion 224 may include a portion that is contoured as to have a leading and/or cutting edge to concentrate and/or direct a shearing force. The wedge and/or blade portion 224 may be oriented such that the leading and/or cutting edge in pointed to the wall of the elongate body 402. The leading and/or cutting edge of the wedge and/or blade portion 224 may have a length that is at least as long as the wall of the elongate body 402 is wide, so that the leading and/or cutting edge of the wedge and/or blade portion 224 may cut through the entire width of the wall of the elongate body 402 in a single pass.

The pushrod 418 may be seated in the lumen 404 such that the leading and/or cutting edge of the wedge and/or blade portion 224 may be aligned with a corresponding structurally compromised portion 426-1 . . . 426-N of the elongate body 402. A user may exert a force load to the plurality of projections 422-1 . . . 411-N which may advance the central body of the pushrod 418 through the lumen to dispense dispensable substances, all while the wedge and/or blade portion 224 extending from the central body of the pushrod 418 clears a path for the plurality of projections 422-1 . . . 411-N to pass through the wall of the elongate body 402 by severing the wall.

Again, while some of the examples described herein are described in relation to severing structurally compromised portions 426-1 . . . 426-N of the elongate body 402 other examples are contemplated and described. For example, the examples may include an elongate body 402 made of a uniform material and/or having a uniform thickness that is strong enough to provide structural integrity during filling, storing, transporting, and dispensing a dispensable substance from the dispensable substance container while simultaneously, being soft enough to be severed by the wedge and/or blade portion 424 under a force load within particular force load threshold values.

The pushrod 418 may be advanced through the lumen 404 of the elongate body 402 to expel a dispensable substance from an opposing end of the elongate body 402. For example, the pushrod 418 may be advanced through the lumen 404 of the elongate body 402 to expel a dispensable substance from a dispensing nozzle mated with a dispensable substance receiving container.

Figure 5:
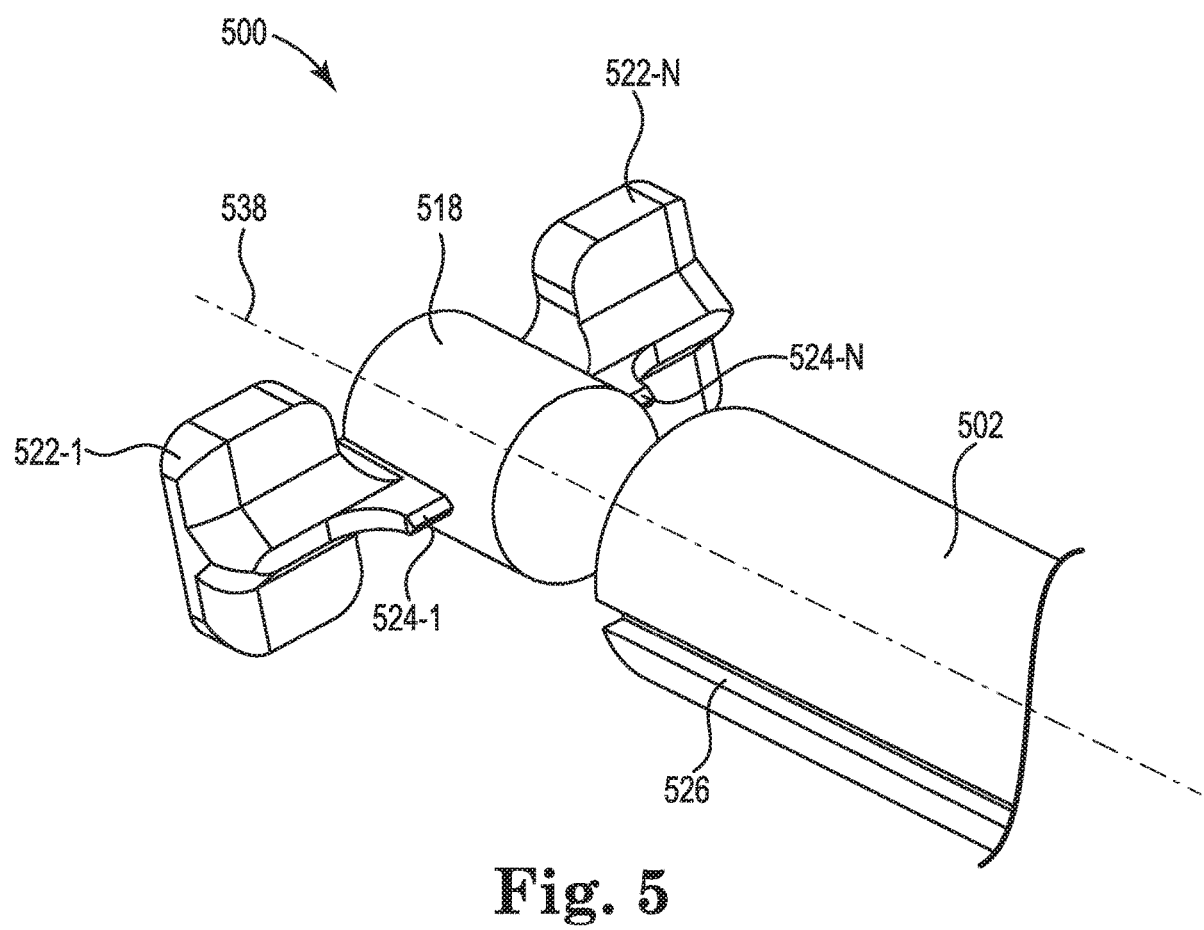
FIG. 5 illustrates a perspective view of a portion of a dispensable substance container.

FIG. 5 illustrates a perspective view of a portion of a dispensable substance container 500. The dispensable container 500 may include an elongate body 502. The elongate body 502 may include a structurally compromised portion 526, although a structurally compromised portion 526 may not be present in some examples.

Also illustrated is pushrod 518. The central body of the pushrod 518 may be an elongate portion having a complementary geometry to a lumen of the elongate body 502. However, the length of the pushrod 518 may have a length along a longitudinal axis 538 that is less than the length of a lumen of the elongate body 502 despite the pushrod 518 being moveable along the entire length of the lumen of the elongate body 502 to reach an opposing end from where it was inserted into the lumen.

The pushrod 518 may include a plurality of projections 522-1 . . . 522-N radiating out from the central body of the pushrod 518. Each one of the plurality of projections 522-1 . . . 522-N may include a respective one of a plurality of wedge and/or blade portions 524-1 . . . 524-N. The leading and/or cutting edge of each one of the plurality of projections 522-1 . . . 522-N may be aligned with a structurally compromised portion 526 of the elongate body 502. The leading and/or cutting edge of each one of the plurality of projections 522-1 . . . 522-N may be pushed through the wall of the elongate body 502 shearing the elongate body into separate portions at the cut and creating a gap for the plurality of projections 522-1 . . . 522-N to continue to travel along with the central body of the pushrod 518 being translated within and through the lumen while remaining outside of the elongate body 502 for continued contact with a user applying the force load.

FIGS. 6 A-D illustrate a system 640 of dispensable substance containers according to examples of the present disclosure, FIGS. 6A-D may illustrate a progression through successive stages of dispensing a dispensable substance from a dispensable substance container 600.

The system 640 may include a dispensable substance container 600. The dispensable substance container 600 may include an elongate body 602. The elongate body 602 may include a wall encompassing a lumen. The lumen may contain a dispensable substance such as a printing substance. In some examples, the elongate body 602 may be made of a uniform material with a uniform thickness and/or a uniform treatment or preparation. In other examples, the elongate body 602 may include a structurally compromised portion 626. The elongate body 602 may extend longitudinally along a length of the elongate body 602.

The dispensable substance container 600 may include a dispensing nozzle 606 at a first end of the elongate body 602. Additionally, the dispensable substance container may include a mating mechanism 620 including walls encompassing the dispensing nozzle 606 to mate with a dispensable substance receiving container 612 in an interlocking fashion to align the dispensing nozzle 606 into the dispensable substance receiving container 612. The dispensable substance receiving container 612 may be a printing substance reservoir cartridge of a printing device.

The system 640 may include a pushrod 618. The pushrod 618 may include a central body of the pushrod 618 that has a complementary geometry to the lumen formed by the elongate body 602. The central body of the pushrod 618 may be dimensioned to fit snuggly but moveably within the lumen of the elongate body 602.

The central body of the pushrod 618 may be moveable longitudinally along the length of the elongate body 602. That is, the central body of the pushrod 618 may be moveable from a second end of an elongate body 602 to an opposing first end of an elongate body 602 within the lumen of the elongate body 602. However, the central body of the pushrod 618 may have a length that is shorter than a length of the lumen and/or elongate body 602. Additionally, the pushrod 618 may be detachable and/or separable from the lumen and/or the elongate body 602.

A projection 622 may project radially outward from the central body of the pushrod 618. The projection 622 may extend from the central body of the pushrod 618 to outside the perimeter of the elongate body 602. For example, the projection 622 may extend outside of the lumen and outside the circumference of the walks of the elongate body 602.

A wedge and/or blade 624 may extend radially out from the central body of the pushrod 618 and/or extend downward from the projection 622. The wedge and/or blade 624 may be aligned with a structurally compromised portion 626 of the elongate body 602, in examples where the elongate body 602 includes such portions. The wedge and/or blade 624 may be positioned over the wall of the elongate body 602 with a leading and/or cutting edge positioned to slice into the elongate body 602.

The central body of the pushrod 618 may be advanced into the lumen of the elongate body 602 by pressing on the projection 622 once the elongate body 602 is mated with the dispensable substance receiving container 612. As the central body of the pushrod 618 in advanced deeper into and through the elongate body 602, the wedge and/or blade 624 may shear a gap 642 into the elongate body 602. In some examples, the wedge and/or blade 624 may shear a gap 642 into the structurally compromised portion 626 of the elongate body 602 as the central body of the pushrod 618 is moved through the lumen in response to a force load applied to a handle-like portion of the projection 622 outside of the wall of the elongate body 602. The handle-like portion of the projection 622 may remain connected to the central body of the pushrod 618 within the lumen through the gap 642 created by the shearing action of the wedge and/or blade 624.

Figure 6A:
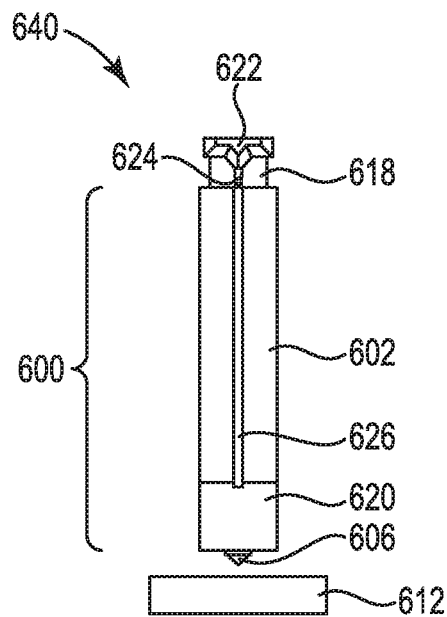
FIGS. 6 A-D illustrate a system of dispensable substance containers according to examples of the present disclosure.
Figure 6B:
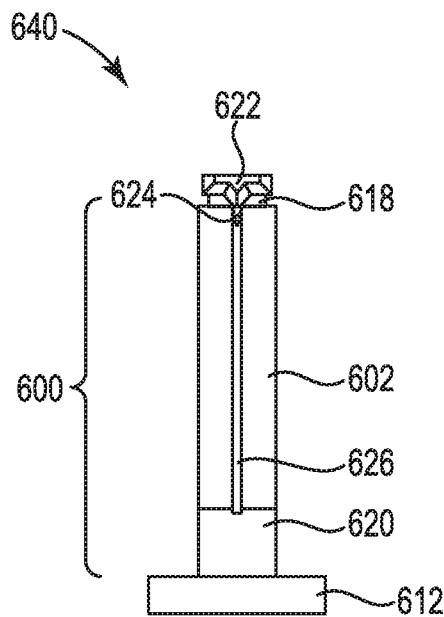
Figure 6C:
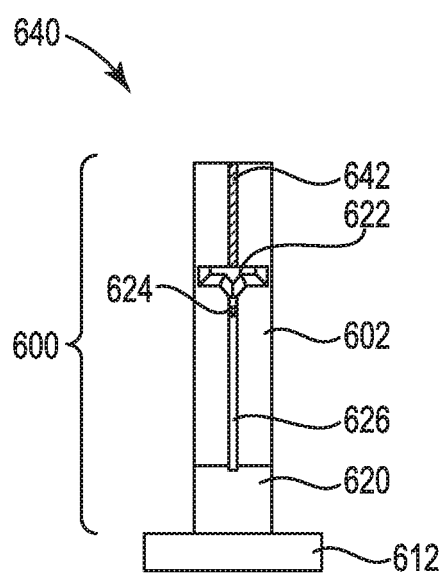
Figure 6D:
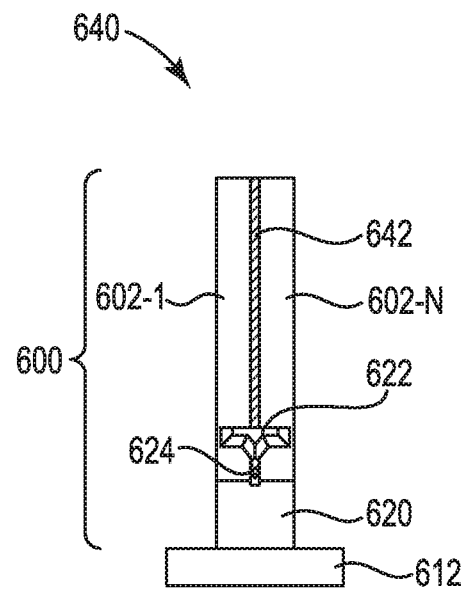

When the central body of the pushrod 618 has traversed the length of the lumen, the dispensable substance may be transferred out of the lumen of the elongate body 602 and transferred to a dispensable substance receiving container 612. As such, the lumen of the elongate body 602 may be substantially emptied of the dispensable substance. As illustrated in FIG. 6D, at such a point, the elongate body 602 may be split along its length into a plurality of portions 602-1 . . . 602-N. As such, the elongate body 602 may be consumable and/or non-reusable. However, the pushrod 618 including the projection 622 and the wedge and/or blade 624, may be removed from the split open elongate body and reused with a next dispensable substance container 600. In some examples, the split apart plurality of portions 602-1 . . . 602-N may be left behind mated to one of a fixed number of filing ports of a dispensable substance receiving container 612. In some examples, the split apart plurality of portions 602-1 . . . 602-N may be removed from the mating mechanism 620 and the mating mechanism may be left behind mated to one of a fixed number of filing ports of a dispensable substance receiving container 612. In some examples, the mating mechanism 620 may not be present and the dispensable substance container 600 may be sheared apart up to the nozzle 602.

Examples described herein may include pushrod that has a length along a longitudinal axis that is less than a length of the lumen of an elongate body along the longitudinal axis. As a result, the packaging, storage, transportation, and shipping of such dispensable substance containers may be easier, cheaper, utilize less materials, and/or subject the dispensable substance containers to less potential damage in the processes. Further, as a result, the dispensable substance containers themselves may be simpler to manufacturer and/or include less material, potentially driving down the cost of manufacturing the dispensable substance containers. Furthermore, a portion of the dispensable substance containers may be fully consumable and/or non-reusable as a result of being severed into portions by the dispensing action. A non-reusable dispensable substance container may not only generate increased demand for a product by making it consumable but may also prevent unintended reuse by a user that may result in contamination of a dispensable substance. Contamination of a dispensable substance such as a printing material that may lead to the introduction of contaminants to a dispensable substance receiving container such as a printing substance reservoir. The contaminants may be introduced from the printing substance reservoir to a device such as a printing device, which may damage the printing device.

The devices and/or systems described herein are not intended to be limited to any specific example described herein. The components of specific examples of devices and/or the systems described herein may be interchangeable with components of other specific examples of devices and/or the systems described herein.

In the foregoing detailed description of the present disclosure, reference is made to the accompanying drawings that form a part hereof, and in which is shown by way of illustration how examples of the disclosure may be practiced. These examples are described in sufficient detail to enable those of ordinary skill in the art to practice the examples of this disclosure, and it is to be understood that other examples may be utilized and that process, electrical, and/or structural changes may be made without departing from the scope of the present disclosure.

The figures herein follow a numbering convention in which the first digit corresponds to the drawing figure number and the remaining digits identify an element or component in the drawing. For example, the reference numeral 102 may refer to element "02" in FIG. 1 and an analogous element may be identified by reference numeral 202 in FIG. 2. Elements shown in the various figures herein can be added, exchanged, and/or eliminated so as to provide a number of additional examples of the present disclosure. In addition, the proportion and the relative scale of the elements provided in the figures are intended to illustrate the examples of the present disclosure and should not be taken in a limiting sense. Further, as used herein, "a" element and/or feature can refer to one or more of such elements and/or features.

What is claimed:

1. A dispensable substance container, comprising:
   an elongate body encompassing a lumen, wherein the lumen is to contain the dispensable sub stance;
   a dispensable substance dispensing nozzle attached to a first end on the elongate body, the dispensable substance dispensing nozzle having a mating mechanism to introduce communication with a dispensable substance receiving container;
   a sealing material within the lumen, wherein the sealing material is moveable, by a pushrod, within the lumen to push the dispensable substance out the dispensing tip; and
   a structurally compromised portion of the elongate body extending along a length of the elongate body, wherein the elongate body is to be severed along the structurally compromised portion by the pushrod into a severed plurality of portions of the elongate body, and the severed plurality of portions is separable from the mating mechanism.

2. The dispensable substance container of claim 1, wherein the pushrod comprises a bladed portion and the structurally comprised portion of the elongate body is to be severed by the bladed portion.

3. The dispensable substance container of claim 1, wherein the structurally compromised portion of the elongate body is a first portion of a wall of the elongate body with a thickness that is less than a thickness of a second portion of the wall of the elongate body.

4. The dispensable substance container of claim 1, wherein a wall of the elongate body includes an inner layer contacting the lumen and an outer layer and the outer layer of the wall has a greater shear strength than the inner layer of the wall.

5. The dispensable substance container of claim 1, wherein the structurally compromised portion of the elongate body is a structurally weakened portion of the wall of the elongate body.

6. The dispensable substance container of claim 1, wherein a non-structurally compromised portion of the elongate body has a greater shear strength than the structurally compromised portion of the elongate body.

7. The dispensable substance container of claim 1, the mating mechanism to align the dispensing nozzle with the dispensable substance receiving container.

8. The dispensable substance container of claim 7, wherein the dispensable substance is a printing substance and the dispensable substance receiving container is a printing substance reservoir cartridge of a printer.

9. A device, comprising:
a pushrod body to seat within a lumen encompassed by a wall of an elongate body of a dispensable substance container, wherein a longitudinal length of the pushrod body is less than half of a longitudinal length of the lumen, the dispensable substance container has a mating mechanism to introduce communication with a dispensable substance receiving container, and the elongate body is severable into a severed plurality of portions separable from the mating mechanism; and
a projection extending from the pushrod body, the projection to extend through the wall of the elongate body when the pushrod body is seated within the lumen.

10. The device of claim 6, wherein the projection is a projection of a plurality of projections extending radially outward from the pushrod body.

11. The device of claim 6, wherein the projection includes a first portion of a first width and a second portion of a second width continuous with the first portion, wherein the first portion connects the second portion to the pushrod body.

12. The device of claim 11, wherein the first width of the first portion is less than the second width of the second portion, the first portion to span through a gap in the wall of the elongate body of the dispensable substance container introduced by an extension off of the projection when the pushrod body is pushed through the lumen to expel a dispensable substance within the lumen.

13. A system, comprising:
a dispensable printing substance container, including:
an elongate body including a wall encompassing a lumen, wherein the lumen is to contain a dispensable printing substance, wherein the elongate body is severable into a severed plurality of portions separable from a mating mechanism to introduce communication with a dispensable substance receiving container, and
a structurally compromised portion of the wall extending longitudinally along a length of the elongate body; and
a pushrod, including:
a central body of the pushrod to seat within the lumen, wherein the central body is moveable longitudinally through the length of the elongate body, and
an extension from the central body to introduce a gap into the structurally compromised portion of the wall when the central body is moved through the lumen in response to a force applied to a handle outside of the wall and connected to the central body through the gap.

14. The system of claim 13, wherein the central body is detachable from the elongate body.

15. The system of claim 13, wherein the elongate body is split into a plurality of portions when the central body is pushed to a first end of the elongate body and the dispensable printing substance is transferred out of the lumen.

* * * * *